(12) United States Patent
Reynolds

(10) Patent No.: US 6,780,844 B1
(45) Date of Patent: Aug. 24, 2004

(54) CALCIUM PHOSPHOPEPTIDE COMPLEXES

(75) Inventor: Eric C. Reynolds, North Balwyn (AU)

(73) Assignee: The University of Melbourne, Parkville (AU)

( * ) Notice: Subject to any disclaimer, the term of this patent is extended or adjusted under 35 U.S.C. 154(b) by 0 days.

(21) Appl. No.: 09/380,738

(22) PCT Filed: Mar. 13, 1998

(86) PCT No.: PCT/AU98/00160

§ 371 (c)(1),
(2), (4) Date: Dec. 6, 1999

(87) PCT Pub. No.: WO98/40406

PCT Pub. Date: Sep. 17, 1998

(30) Foreign Application Priority Data

Mar. 13, 1997 (AU) ............................................ PO 5662

(51) Int. Cl.[7] ........................... A61K 38/03; A61K 7/16
(52) U.S. Cl. .............................. 514/7; 514/12; 514/13; 514/14; 514/17; 530/352; 530/360; 424/49; 424/52; 424/57
(58) Field of Search ................................ 514/7, 12–14, 514/17; 530/352, 360; 424/49, 52, 57

(56) References Cited

U.S. PATENT DOCUMENTS 5,981,475 A * 11/1999 Reynolds ....................... 514/6

FOREIGN PATENT DOCUMENTS

| WO | WO 82/03008 | 9/1982 |
|----|-------------|--------|
| WO | WO 87/07615 | 12/1987 |
| WO | WO 94/00146 | 6/1994 |
| WO | WO 96/29340 | 9/1996 |

OTHER PUBLICATIONS

Shidaka, et al., "A New Method for Study of the Formation and Transformation of Calcium Phosphate Precipitates: Effects of Several Chemical Agents and Chinese Folk Medcines," *Archives of Oral Biol.*, 36:1 49–54 (1991).

Reynolds, E.C. "Dairy Products and Dental Health," *Proceedings of the Nutrition Society of Australia* 19 95–102 (1995).

Huo, et al., A H–NMR Study of the Casein Phosphopeptide @ Casein (59–79) *Biochimica et Biophysica Acta*, 1247 201–208 (1995).

Reynolds, et al., "Anticariogenicity of Clcium Phosphate Complexes of Tryptic Casein Phosphopeptides in the Rat," *J Dent Res*, 74(6): 1272–1279 (1995).

Holt, et al., "Ability of a β–casein Phosphopeptide to Modulate the Precipitation of Calcium Phosphate by Forming Amorphous Dicalcium Phosphate Nanoclusters," *Biochem J.*, 314, 1035–1039 (1996).

Adamson, et al., "The Analysis of Multiple Phosphoseryl–containing Casein Peptides using Capillary Zone Electrophoresis," *J. of Chromatography*, 646 391–396 (1993).

Adamson, et al., "Characterization of Casein Phosphopeptides Prepared Using Alcalase: Determination of Enzyme Specificity," *Enzyme and Microbial Tech.*, 19 202–207 (1996).

Reynolds, E, C., "Remineralization of Enamel Subsurface Lesions by Casein Phosphopeptide–stabilized Calcium Phosphate Solutions," *J Dent Res.*, 76:9 1587–1595 (1997).

Wilkiel, et al., "Hydroxyapatite Mineralization and Demineralization in the Presence of Synthetic Phosphorylated Pentapeptides," *Archives of Oral Biology*, 39:8 715–721 (1994).

* cited by examiner

*Primary Examiner*—Christopher S. F. Low
*Assistant Examiner*—David Lukton
(74) *Attorney, Agent, or Firm*—Foley & Lardner

(57) ABSTRACT

Phosphopeptides containing the Ser(P) cluster sequence motif Ser(P)-Ser(P)-Ser(P)-Glu-Glu- can stabilize their own weight in amorphous calcium phosphate (ACP) and amorphous calcium fluoride phosphate (ACFP). The amorphous phases stabilized by the phosphopeptides are an excellent delivery vehicle to co-localise calcium, fluoride, and phosphate ions at the tooth surface in a slow-release amorphous form producing superior anticaries efficacy. These amorphous phases stabilized by the phosphopeptides also have utility as dietary supplements to increase calcium bioavailability and to help prevent diseases associated with calcium deficiencies.

27 Claims, No Drawings

CALCIUM PHOSPHOPEPTIDE COMPLEXES

The present invention relates to novel complexes in which amorphous calcium phosphates are stabilised by phosphopeptides. These complexes have anti-cariogenic effects, and may also be used as dietary supplements to increase calcium bioavailability and to heal or prevent diseases associated with calcium deficiencies. Methods of making the complexes of the invention and of treatment or prevention of dental caries, calcium malabsorption, and bone diseases are also provided

BACKGROUND

Dental Caries

Dental caries is initiated by the demineralisation of hard tissue on the teeth by organic acids produced from fermentation of dietary sugar by dental plaque odontopathogenic bacteria Even though the prevalence of dental caries has deceased through the use of fluoride in most developed countries, the disease =as a major public health problem. The estimated economic burden of treating dental caries in Australia in 1991 was $471 million, being higher an that for other diet-related diseases including coronary heart disease, hypertension or stroke.

In developing countries where the availability of industrialised food products is increasing, prevalence of dental caries is also increasing. Recent studies have highlighted a number of socio-demographic variables associated with the risk of developing caries; high risk is associated with ethnicity and low socio-economic status. The level of high-risk individuals has remained constant even though the overall severity and prevalence of disease in the community has decreased. Dental caries is therefore, still a major public health problem, particularly in ethnic and lower socioeconomic groups. This highlights the need for a non-toxic, anticariogenic agent that could supplement the effects of fluoride to fit lower the incidence of dental caries. An agent which would reduce the dose of fluoride required to reduce the incidence of caries would be particularly desirable in view of community anxiety about fluoride, and in view of the fact that fluorosis can develop even at currently used doses.

The food group most recognised as exhibiting anticaries activity is dairy products (milk, milk concentrates, powders and cheeses). U.S. Pat. No. 5,130,123 discloses the component responsible for this anticariogenic activity as casein. However, the use of casein as an anticariogenic agent is precluded by adverse organoleptic properties and the very high levels required for activity.

Preliminary investigations determined that tryptic casein phosphopeptides contributed to the anticariogenic activity and this was made subject of U.S. Pat. No. 5,015,628. In particular, peptides Bos $\alpha_{s1}$-casein X-5P (f59–79) (SEQ ID NO: 1, Bos β-casein X-4P (f1–25) (SEQ ID: NO: 2), Bos $\alpha_{s2}$-casein X-4P (f46–70) (SEQ ID NO: 3) and Bos $\alpha_{s2}$-casein X-4P (f1–21) (SEQ ID NO: 4) were disclosed in U.S. Pat. 5,015,628 as follows:

(SEQ ID NO: 1) Gln$^{59}$-Met-Glu-Ala-Glu-Ser(P)-Ile-Ser(P)-Ser(P)-Glu-Ile-Val-Pro-Asn-Ser(P)-Val-Glu-Gln-Lys$^{79}$. $\alpha_{s1}$(59–79)

(SEQ ID NO: 2) Arg$^{1}$-Glu-Leu-Glu-Glu-Leu-Asn-Val-Pro-Gly-Glu-Ile-Val-Glu-Ser(P)-Leu-Ser(P)-Ser(P)-Ser(P)-Glu-Glu-Ser-Ile-Thr-Arg$^{25}$. β(1–25)

(SEQ ID NO: 3) Asn$^{46}$-Ala-Asn-Glu-Glu-Glu-Tyr-Ser-Ile-Gly-Ser(P)-Ser(P)-Ser(P)-Glu-Glu-Ser(P)-Ala-Glu-Val-Ala-Thr-Glu-Glu-Val-Lys$^{70}$. $\alpha_{s2}$(46–70)

(SEQ ID NO: 4) Lys$^{1}$-Asn-Thr-Met-Glu-His-Val-Ser(P)-Ser(P)-Ser(P)-Glu-Glu-Ser-Ile-Ile-Ser(P)-Gln-Glu-Thr-Tyr-Lys$^{21}$. $\alpha_{s2}$(1–21)

The preliminary determination of the above phosphopeptides for use in combination with CaHPO$_4$ and hydroxyaptite provided novel peptides having anticariogenic properties. However, subsequent investigations have determined that the Ser(P) cluster sequence motif within the previous disclosed phosphopeptides have the unexpected ability to stabilize their own weight in amorphous calcium phosphate. The ability of the above phosphopeptides and in particular the Ser(P) motif to stabilise amorphous calcium phosphate was quite unexpected and neither disclosed or taught in any publications known to the Applicants. We have now found that the amorphous form of calcium phosphate Ca$_3$(PO$_4$)$_{1.87}$(HPO$_4$)$_{0.2}$xH$_2$O where x≧1 stabilised by the casein phosphopeptides is the most soluble, basic form of non-crystalline calcium phosphate and a superior form of calcium phosphate which prevents caries and increases calcium bioavailability. Amorphous calcium phosphate (ACP) must be formed by careful titration of Ca ions (eg CaCl$_2$) and phosphate ions (eg Na HPO$_4$) while maintaining the pH above 7 (preferably 9.0) in the presence of the phosphopeptide. As the ACP is formed, the phosphopeptide binds to the nascent nuclei and stabilises the ACP as a phosphopeptide-ACP complex. Without the phosphopeptide, the ACP will precipitate out of solution and transform within minutes into, the most stable calcium phosphate phase, crystalline hydroxyapatite (HA). HA, by being insoluble has limited anticariogenic activity and presents calcium in a poorly bioavailable form. The acidic phase of calcium phosphate CaHPO$_4$, while certainly being more soluble than hydroxyapatite, is poorly bound by the phosphopeptide and poorly localised at the tooth surface and therefore also has limited anticariogenic activity. The unexpected ability of the aforementioned phosphopeptides and in particular Ser(P) cluster motif to stabilize amorphous calcium phosphate was not disclosed or taught in U.S. Pat. No. 5,015,628 and provides for the first time a reliable and effective method of producing a stabilized amorphous calcium phosphate complex having distinct and novel advantages in calcium treatments and delivery. U.S. Pat. No. 5,015,628 does not disclose the unique amorphous calcium fluoride phosphate phase Ca$_8$(PO$_4$)$_5$F x H$_2$O where x≧1 which we have now found to be stabilised by the above phosphopeptides and can be localised at the tooth surface to provide superior anticaries efficacy. This unexpected ability to stabilize amorphous calciun phosphate forms the basis of the instant invention.

SUMMARY OF THE INVENTION

In one aspect, the invention provides a stable calcium phosphate complex, comprising amorphous calcium phosphate or a derivative thereof stabilized by a phosphopeptide, wherein said phosphopeptide comprises the sequence Ser(P)-Ser(P)-Ser(P)-Glu-Glu-(SEQ ID NO: 5).

In one embodiment, the complex may include phosphopeptide stabilized amorphous calcium fluoride phosphate.

The phosphopeptide (PP) may be from any source; it may be obtained by tryptic digestion of casein or other phosphoacid rich proteins such as phosphitin, or by chemical or recombinant synthesis, provided that it comprises the core sequence -Ser(P)-Ser(P)-Ser(P)-Glu-Glu-(SEQ ID NO: 5). The sequence flanking this core sequence may be any sequence. However, those flanking sequences in $\alpha_{s1}$(59–79) (SEQ ID NO: 1), β(1–25) (SEQ ID NO: 2), $\alpha_{s2}$(46–70 (SEQ ID NO: 3) and $\alpha_{s2}$(1–21) (SEQ ID NO: 4) are preferred. The flanking sequences may optionally be modified by deletion, addition or conservative substitution of one or more residues. The amino acid composition and sequence of the flanking region are not critical as long as the conformation of the peptide is maintained and that all phosphoryl and carboxyl groups interacting with calcium ions are maintained as the preferred flanking regions appear to contribute to the structural action of the motif.

When the complex takes the form of phosphopeptide stabilized amorphous calcium fluoride phosphate, the calcium fluoride phosphate may be of the approximate formula $[Ca(PO_4)_5 \, Fx \, H_2O]$ wherein $x \geq 1$.

The complex may firer include $HPO_4$ as a minor optional component to the complex. The HP04 is believed to act as a coating for the ACP cluster. When the complex takes the alternative form of a stable soluble alkaline calcium phosphate complex including stabilized amorphous calcium phosphate, the amorphous calcium phosphate may be of the approximate formula $[Ca_3(PO_4)_2 \, x \, H_2O]$ wherein $x \geq 1$.

The complex may firther include $HPO_4$ as a minor optional component. The complex most preferably has a pH of about 9.0.

The phosphopeptide (PP) may be from any source; it may be obtained by tryptic digestion of casein or other phosphoacid rich proteins such as phosphitin, or by chemical or recombinant synthesis, provided that it comprises the core sequence -Ser(P)-Ser(P)-Ser(P)-Glu-Glu-. The sequence flanking this core sequence may be any sequence. However, those flanking sequences in $\alpha_{s1}(59-79)$ [1], $\beta(1-25)$ [2], $\alpha_{s2}(46-70)$ [3] and $\alpha_{s2}(1-21)$ [4] are preferred. The flanking sequences may optionally be modified by deletion, addition or conservative substitution of one or more residues. The amino acid composition and sequence of the flanking region are not critical as long as the conformation of the peptide is maintained and that all phosphoryl and carboxyl groups interacting with calcium ions are maintained as the preferred flanking regions appear to contribute to the structural action of the motif.

The complex formed preferably has the formula $[(PP)(CP)_8]_n$ where n is equal to or greater than 1, for example, 6. The complex formed may be a colloidal complex.

The phosphopeptide binds to the ACP cluster to produce a metastable solution in which growth of ACP to a size that initiates nucleation and precipitation is prevented. In this way, calcium and other ions such as fluoride ions can be localised, for instance at a surface on a tooth to prevent demineralisation and prevent formation of dental caries.

Thus, in a second aspect, the invention provides a stable calcium phosphate complex as described above, which complex acts as a delivery vehicle that co-localises ions including, but not limited to calcium, fluoride and phosphate ions at a target site. In a preferred embodiment, the complex is in a slow-release amorphous form that produces superior anti-caries efficacy.

In a particularly preferred embodiment of the invention, the stable calcium complex is incorporated into dentifrices such as toothpaste, mouth washes or formulations for the mouth to aid in the prevention and/or treatment of dental caries or tooth decay. The calcium complex may comprise 0.05–50% by weight of the composition, preferably 1.0–50%. For oral compositions, it is preferred that the amount of the CPP-ACP and/or CPP-ACFP administered is 0.05–50% by weight, preferably 1.0%–50% by weight of the composition. The oral composition of this invention which contains the above-mentioned agents may be prepared and used in various forms applicable to the mouth such as dentifrice including toothpastes, toothpowders and liquid dentifrices, mouthwashes, troches, chewing gums, dental pastes, gingival massage creams, gargle tablets, dairy products and other foodstuffs. The oral composition according to this invention may flirter include additional well known ingredients depending on the type and form of a particular oral composition.

In certain highly preferred forms of the invention the oral composition may be substantially liquid in character, such as a mouthwash or rinse. In such a preparation the vehicle is typically a water-alcohol mixture desirably including a humnectant as described below. Generally, the weight ratio of water to alcohol is in the range of from about 1:1 to about 20:1. The total amount of water-alcohol mixture in this type of preparation is typically in the range of from about 70 to about 99.9% by weight of the preparation. The alcohol is typically ethanol or isopropanol. Ethanol is preferred.

The pH of such liquid and other preparations of the invention is generally in the range of from about 5 to about 9 and typically from about 7.0–9.0. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc).

In other desirable forms of this invention, the oral composition may be substantially solid or pasty in character, such as toothpowder, a dental tablet or a toothpaste (dental cream) or gel dentifrice. The vehicle of such solid or pasty oral preparations generally contains dentally acceptable polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, hydrated alumina, calcined alumina, aluminum silicate, zirconium silicate, silica, bentonite, and mixtures thereof. Other suitable polishing material include the particulate thermosetting resins such as melamine-, phenolic, and urea-formaldehydes, and cross-linked polyepoxides and polyesters. Preferred polishing materials include crystalline silica having particle sized of up to about 5 microns, a mean particle size of up to about 1.1 microns, and a surface area of up to about 50,000 $cm^2$/gm., silica gel or colloidal silica, and complex amorphous alkali metal aluminosilicate.

When visually clear gels are employed, a polishing agent of colloidal silica, such as those sold under the trademark SYLOID as Syloid 72 and Syloid 74 or under the trademark SANTOCEL as Santocel 100, alkali meal alumino-silicate complexes are particularly usefull since they have refractive indices close to the refractive indices of gelling agent-liquid (including water and/or humectant) systems commonly used in dentifrices.

Many of the so-called "water insoluble" polishing materials are anionic in character and also include small amounts of soluble material. Thus, insoluble sodium metaphosphate may be formed in any suitable manner as illustrated by Thorpe's Dictionary of Applied Chemistry, Volume 9, 4th Edition, pp. 510–511. The forms of insoluble sodium metaphosphate known as Madrell's salt and Kurrol's salt are farther examples of suitable materials. These metaphosphate salts exhibit only a minute solubility in water, and therefore are commonly referred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired The insoluble alkali metal metaphosphate is typically employed in powder form of a particle size such that no more than 1% of the material is larger than 37 microns.

The polishing material is generally present in the solid or pasty compositions in weight concentrations of about 10% to about 99%. Preferably, it is present in amounts from about 10% to about 75% in toothpaste, and from about 70%/o to about 99% in toothpowder. In toothpastes, when the polishing material is silicious in nature, it is generally present in amount of about 10–30% by weight, Other polishing materials are typically present in amount of about 30–75% by weight.

In a toothpaste, the liquid vehicle may comprise water and humectant typically in an amount ranging from about 10% to about 80% by weight of the preparation. Glycerine, propylene glycol, sorbitol and polypropylene glycol exemplify suitable humectants/carriers. Also advantageous are liquid mixtures of water, glycerine and sorbitol. In clear gels where the refractive index is an important consideration, about 2.5–30% w/w of water, 0 to about 70% w/w of glycerine and about 20–80% w/w of sorbitol are preferably employed.

Toothpaste, creams and gels typically contain a natural or synthetic thickener or gelling agent in proportions of about 0.1 to about 10, preferably about 0.5 to about 5% w/w. A suitable thickener is synthetic hectorite, a synthetic colloidal magnesium alkali metal silicate complex clay available for example as Laponite (e.g. CP, SP 2002, D) marketed by Laporte Industries Limited. Laponite D is, approximately by weight 58.00% $SiO_2$, 25.40% MgO, 3.05% $Na_2O$, 0.98% $Li_2O$, and some water and trace metals. Its true specific gravity is 2.53 and it has an apparent bulk density of 1.0 g/ml at 8% moisture.

Other suitable thickeners include Irish moss, iota carrageenan, gum tragacanth, starch, polyvinylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244). Solubilizing agents may also be included such as humectant polyols such propylene glycol, dipropylene glycol and hexylene glycol, cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate.

It will be understood that, as is conventional, the oral preparations are to be sold or otherwise distributed in suitable labelled packages. Thus, a jar of mouthrinse will have a label describing it, in substance, as a mouthrinse or. mouthwash and having directions for its use; and a toothpaste, cream or gel will usually be in a collapsible tube, typically aluminium, lined lead or plastic, or other squeeze, pump or pressurized dispenser for metering out the contents, having a label describing it, in substance, as a toothpaste, gel or dental cream.

Organic surface-active agents are used in the compositions of the present invention to achieve increased prophylactic action, assist in achieving thorough and complete dispersion of the active agent throughout the oral cavity, and render the instant compositions more cosmetically acceptable. The organic surface-active material is preferably anionic, nonionic or ampholytic in nature and preferably does not interact with the active agent. It is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfite, alkyl aryl sulfonates such as sodium dodecyl benzene sulfonate, higher alkylsulfo-acetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarconite compounds in the oral compositions of the present invention is particularly advantageous since these materials exhibit a prolonged marked effect in the inhibition of acid formation in the oral cavity due to carbohydrates breakdown in addition to exerting some reduction in the solubility of tooth enamel in acid solutions. Examples of water-soluble nonionic surfactants suitable for use are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic materials).

The surface active agent is typically present in amount of about 0.1–5% by weight. It is noteworthy, that the surface active agent may assist in the dissolving of the active agent of the invention and thereby diminish the amount of solibilizing humectant need.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired.

Any suitable flavouring or sweetening material may also be employed. Examples of suitable flavouring constituents are flavouring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, AMP (aspartyl phenyl alanine, methyl ester), saccharine, and the like. Suitably, flavour and sweetening agents may each or together comprise from about 0.1% to 5% more of the preparation In the preferred practice of this invention an oral composition according to this invention such as mouthwash or dentifrice containing the composition of the present invention is preferably applied regularly to the gums and teeth, such as every day or every second or third day or preferably from 1 to 3 times daily, at a pH of about 4.5 to about 9, generally about 7.0 to about 9, for at least 2 weeks up to 8 weeks or more up to a lifetime.

The compositions of this invention can also be incorporated in lozenges, or in chewing gum or other products, e.g. by stirring into a warm gum base or coating the outer surface of a gum base, illustrative of which may be mentioned jelutong, rubber latex, vinylite resins, etc., desirably with conventional plasticizers or softeners, sugar or other sweeteners or such as glucose, sorbitol and the like.

In another embodiment, the complex of the invention is formulated to form a dietary supplement preferably comprising 0.1–100% w/w, more preferably 1–50% w/w, most preferably 1–10% and particularly 2% w/w. The complex may also be incorporated into food products.

Accordingly, in a third sect the invention provides compositions including pharmaceutical compositions comprising the calcium complex as described together with a pharmaceutically-acceptable carrier. Such compositions may be selected from the group consisting of dental, anticariogenic compositions, therapeutic compositions and dietary supplements. Dental compositions or therapeutic compositions may be in the form of a gel, liquid, solid, powder, cream or lozenge. Therapeutic compositions may also be in the form of tablets or capsules.

In a fourth aspect, there is provided a method of treating or preventing dental caries or tooth decay comprising the step of administering a complex or composition of the invention to the teeth or gums of a subject in need of such treatments. Topical administration of the complex is preferred.

In a fifth aspect, the invention relates to methods of treating one or more conditions related to calcium loss from the body, especially from the bones, calcium deficiency, calcium malabsorption, or the like. Examples of such conditions include, but are not limited to, osteoporosis and osteomalacia. In general any condition which can be improved by calcium bioavailability is contemplated In a sixth aspect, the invention also provides a method of producing a stable complex of calcium phosphate as described above, comprising the step of:

(i) obtaining a solution of phosphopeptide having a pH of about 9.0;

(ii) admixing (i) with solutions comprising calcium, and inorganic phosphate and optionally fluoride at a pH of about 9.0;

(iii) filtering the mixture resulting from step (ii), and (iv) drying to obtain the said complex.

The complexes of the invention are useful as calcium supplements in subjects in need of stimulation of bone growth, for example subjects undergoing frature repair, joint replacement, bone grafts, or craniofacial surgery.

These complexes are also useful as dietary supplements m subjects who for any reason, such as dietary intolerance, allergy, or religious or cultural factors, are unable or unwilling to consume dairy products in an amount sufficient to supply their dietary calcium requirements.

It will be clearly understood tat, although this specification refers specifically to applications in humans, the invention is also useful for veterinary purposes. Thus in all aspects the invention is useful for domestic animals such as cattle, sheep, horses and poultry; for companion animals such as cats and dogs; and for zoo animals.

DETAILED DESCRIPTION OF THE INVENTION

The invention will now be described in detail by way of reference only to the following non-limiting Examples.

EXAMPLE 1

Preparation of CPP-ACP and CPP-ACFP

A. Preparation of CPP-ACP

A 10% w/v casein (Murray Goulburn, Victoria, Australia) or caseinate solution was prepared at pH 8.0 and then digested with trypsin at 0.2% w/w of the casein for 2 h at 50° C. with the pH controlled to 8.0±0.1 by NaOH addition. After digestion the solution was adjusted to pH 4.6 by the addition of HCl and the precipitate removed by centrifugation or microfiltration. However, the solution can also be clarified by microfiltration at pH 8.0 without acidification. The supernatant or microfiltrate was then adjusted to pH 9.0 with NaOH, then $CaCl_2$ (1.6 M) and $Na_2HPO_4$ (1 M) at pH 9.0 were added slowly ($\leq$1% vol per min) with constant agitation with the pH held constant at 9.0±0.1 by NaOH addition. $CaCl_2$ and sodium phosphate were added to the final concentrations of 100 mM and 60 mM respectively. Following the addition of the calcium and phosphate solutions, the solution was microfiltered through a 0.1 or 0.2 µm microfilter (ceramic or organic) to concentrate the solution five fold. The retentate was then diafiltered with one to five volumes of distilled water. The retentate after diafiltration was spray-dried to produce a white powder that was 50% CPP and 40% ACP and residue water. Analysis of the CPP of the CPP-ACP complex by reversed-phase HPLC, sequence analysis and mass spectrometry revealed that the only peptides that are capable of stabilizing the amorphous calcium phosphate and retained during the microfiltration and diafiltration are Bos $\alpha_{s1}$-casein X-5P (f59–79) (SEQ ID NO: 1), Bos β-casein X4P (f1–25) (SEQ ID NO: 2), Box $\alpha_{s2}$-casein X-4P (f46–70) (SEQ ID NO: 3) and Bos $\alpha_{s2}$-casein X-4P (f1–21) (SEQ ID NO: 4) and truncated and heat modified forms of these peptides.

B. Preparation of CPP-ACFP

A 10% w/v casein or caseinate solution was prepared at pH 8.0±0.1 and then digested with trypsin at 0.2% w/w of the casein for 2 h at 50° C. After digestion the solution was adjusted to pH 4.6 by the addition of HCl and the precipitate removed by centrifugation or microfiltration. However the solution can also be clarified by microfiltration at pH 8.0 without acidification. The supernatant or microfiltrate was then adjusted to pH 9.0 with NaOH, then $CaCl_2$ (1.6 M), $Na_2HPO_4$ (1 M) at pH 9.0 and 200 mM NaF were added slowly ($\leq$1% vol per min) with constant agitation with the pH held constant at 9.0±0.1 by NaOH addition. $CaCl_2$, sodium phosphate and NaF were added to the final concentations of 100 mM, 60 mM and 12 mM respectively. Following the addition of the calcium, phosphate and fluoride solutions the solution was microfiltered through a 0.1 or 0.2 µm microfilter (ceramic or organic) to concentrate the solution five fold. The retentate was then diafiltered with one to five volumes of distilled water. The retentate after diafiltration was spraydried to produce a white powder that was 50% CPP and 40% ACFP and residue water.

The powdered CPP-ACFP was then reconstituted in distilled water to produce highly concentrated solutions. For example, a 10% w/v CPP-ACFP solution containing 640 mM Ca, 400 mM phosphate and 80 mM F (1,520 ppm F) at pH 9.0 has been prepared as well as a 20% CPP gel containing 1.28 M Ca, 800 mM phosphate and 160 mM F (3,040 ppm F) at pH 9.0. This solution and gel exhibit a significantly grater anticariogenicity relative to the fluoride alone and therefore are superior additives to toothpaste and mouthwash and for professional application to improve the efficacy of the current fluoride-containing dentifices and professionally-applied products.

EXAMPLE 2

Structural Studies of CCP-ACP

A. Structure and Interaction of CCP-ACP

Casein phosphopeptides containing the Ser(P) cluster, i.e. the core sequence motif Ser(P)-Ser(P)-Ser(P)-Glu-Glu- (SEQ ID NO: 5), have a marked ability to stabilize calcium phosphate in solution. Solutions containing 0.1% w/v $\alpha_{s1}$ (59–79) (SEQ ID NO: 1) at various pH, calcium and phosphate concentrations, but constant ionic strengths were used to characterize the peptide's interaction with calcium phosphate. The peptide was found to maximally bind 24 Ca and 16 Pi per molecule as shown in Table 1.

The ion activity products for the various calcium phosphate phases [hydroxyapatite (HA); octacalcium phosphate (OCP); tricalcium phosphate (TCP); amorphous calcium phosphate (ACP); and dicalcium phosphate dihydrate (DCPD) were determined from the free calcium and phosphate concentrations at each pH using a computer program that calculates the ion activity coefficients through the use of the expanded Debye-Hückel equation and takes into account the ion pairs $CaHPO_4^°$, $CaH_2PO_4^+$, $CaPO_4^-$ and $CaOH^+$ the dissociation of $H_3PO_4$ and $H_2O$ and the ionic strength. The only ion activity product that significantly correlated with calcium phosphate bound to the peptide independently of pH was that corresponding to ACP $[Ca_3(PO_4)_{1.87}(HPO_4)_{.02x}H_2O]$ indicating that this is the phase stabilized by $\alpha_{s1}(59-79)$ SEQ ID NO: 1. The peptide $\alpha_{s1}(59-79)$ (SEQ ID NO: 1) binds to forming ACP clusters producing a metastable solution preventing ACP growth to the critical size required for nucleation and precipitation. The binding of $\alpha_{s1}(59-79)$ (SEQ ID NO: 1) to ACP results in the formation of colloidal complexes with the unit formula $[\alpha_{s1}(59-79)$ (SEQ ID NO: 1)$(ACP)_8]_n$ where n is equal to or greater than one. It is likely that the predominant form is n=6 as $\alpha_{s1}(59-79)$ (SEQ ID NO: 1) cross-linked with glutaraldehyde in the presence of ACP runs as a hexamer on polyacrylamide gel electrophoresis. Interestingly, the synthetic octapeptide $\alpha_{s1}(63-70)$ AcGlu-Ser(P)-Ile-Ser(P)-Ser(P)-Ser(P)-Glu-GluNHMe (SEQ ID NO: 6) only binds 12 Ca and 8 Pi per molecule i.e. $(ACP)_4$ and the synthetic peptides corresponding to the N-terminus $\alpha_{s1}$ (59–63), Gln-Met-Glu-Ala-Glu (SEQ ID NO: 7) and the C-terminus $\alpha_{s1}(71-78)$, Ile-Val-Pro-Asn-Ser(P)-Val-Glu-Gln (SEQ ID NO: 8) of $\alpha_{s1}(59-79)$ did not bind calcium phosphate as shown in Table 1. These results indicate that conformational specificity is essential for full ACP binding.

B. NMR Studies

Protein flexibility in solution is the outstanding characteristic to emerge from spectroscopy studies on proteins containing the Ser(P) cluster sequence (-Ser(P)-Ser(P)-Ser(P)-) such as phosvitin from egg yolk and phosphophoryn from tooth dentine. Phosphorylation appears to destabilise secondary and tertiary structure rather than promote higher levels of ordering. However, flexible phosphorylated sequences adapt more regular conformations when bound to calcium phosphate. Optical rotatory dispersion (ORD), circular dichroism (CD), hydrodynamic and $^{31}P$ nuclear magnetic resonance (NMR) measurements of the caseins all indicate that $\alpha_{s1}$-casein and β-casein have a rather open structure in solution with many amino acid side chains exposed to solvent and relatively flexible. $^{31}P$-NMR relaxation measurements indicate that Ser(P) residues are relatively mobile in β-casein.

We have demonstrated medium- and long-range nuclear Overhauser enhancements (nOes) in 2D $^1H$ NMR spectra of $\alpha_{s1}(59-79)$ (SEQ ID NO: 1) in the presence of $Ca^{2+}$ indicating a conformational preference. Two structured regions were identified. Residues Val72 to Val76 are implicated in a α-turn conformation. Residues Glu61 to Ser(P)67, which extend over part of the Ser(P) cluster motif -Ser(P)-Ser(P)-Ser(P)-Glu-Glu- (SEQ ID NO: 5) are involved in a loop-type structure. 2D NMR studies on β-casein(1–25) (SEQ ID NO: 2) in the presence of calcium have shown a medium range nOe in the -Ser(P)[17]-Ser(P)-Ser(P)-Glu-Glu[21]- (SEQ ID NO: 5) motif region between the CαH of Ser(P)[18] and NH of Blu[20]. Further medium range noes include one between the CαH of Ser[22] and NH of Thr[24]. Evidence from the $^1H$ NMR spectra of $\alpha_{s2}$-casein(1–21) [4] have shown that several residues including those around the -Ser(P)-Ser(P)-Ser(P)-Glu-Glu- (SEQ ID NO: 5) are perturbed. Furthermore, there are medium range nOes between NH of Ser(P)[8] and NH of GLU[10]. This is yet another example of a medium range nOe in the -Ser(P)-Ser(P)-Ser(P)-Glu-Glu- (SEQ ID NO: 5) motif. Other examples of medium range nOes include that between the NH of Ile[14] and NH of Ser(P)[16].

In summary the NMR data indicates that preferred conformations exist for these peptides in the presence of calcium ions. Molecular modeling of both $\alpha_{s1}(59-79)$ (SEQ ID NO: 1) and β(1–25) (SEQ ID NO: 2) using the constraints derived from the NMR spectroscopy have indicated that the peptides adopt conformations that allow both glutamyl and phosphoseryl side chains of the cluster motif -Ser(P)-Ser(P)-Ser(P)-Glu-Glu (SEQ ID NO: 5) to interact collectively with calcium ions of the ACP.

The relationship between CPP structure and interaction with amorphous calcium phosphate was investigated using a series of synthetic peptide homologues and analogues indicated in Table 1. These studies showed that the cluster sequence-Ser(P)-Ser(P)-Ser(P)-Glu-Glu- (SEQ ID NO: 5) was mainly responsible for the interaction with ACP and that all three contiguous Ser(P) residues are required for maximal interaction with ACP.

TABLE 1

Calcium Phosphate Binding by CPP and Synthetic Homologues and Analogues

| | $V_{ca}$ mol/mol | $V_{PI}$ mol/mol | Ca/P |
|---|---|---|---|
| (SEQ ID NO: 5)ΣΣΣEE | 9 | 6 | 1.5 |
| (SEQ ID NO: 9)SΣΣEE | 2 | 1 | 2.0 |
| (SEQ ID NO: 10)EΣΣEE | 2 | 1 | 2.0 |
| (SEQ ID NO: 11)DΣΣEE | 2 | 1 | 2.0 |
| (SEQ ID NO: 12)θθθEE | 9 | 6 | 1.5 |
| (SEQ ID NO: 13)SθθEE | 2 | 1 | 2.0 |
| (SEQ ID NO: 14)AΣAE | 0 | 0 | |
| (SEQ ID NO: 15)IAΣAEA | 0 | 0 | |
| (SEQ ID NO: 16)EAIAΣAEA | 0 | 0 | |
| (SEQ ID NO: 17)AΣAΣAE | 0 | 0 | |
| (SEQ ID NO: 18)AΣAΣAΣAE | 2 | 1 | 1.5 |
| (SEQ ID NO: 19)AΣAΣAΣAΣAE | 6 | 4 | 1.5 |
| (SEQ ID NO: 1)$\alpha_{a1}$ (59–79) QMEAEΣIΣΣΣEEIVPNΣVEQK | 24 | 16 | 1.5 |
| (SEQ ID NO: 6)$\alpha_{a1}$ (63–70) EΣIΣΣΣEE | 12 | 8 | 1.5 |
| (SEQ ID NO: 5)$\alpha_{a1}$ (66–70) ΣΣΣEE | 9 | 6 | 1.5 |
| (SEQ ID NO: 8)$\alpha_{a1}$ (71–78) IVPNΣVEQ | 0 | 0 | |
| (SEQ ID NO: 7)$\alpha_{a1}$ (59–63) QMEAE | 0 | 0 | |
| (SEQ ID NO: 2)β (1–25) RELEELNVPGEIVEΣLΣΣΣEESITR | 24 | 16 | 1.5 |
| (SEQ ID NO: 20)β (14–21) EΣLΣΣΣEE | 12 | 8 | 1.5 |

Σ = Ser(P),
θ = Thr(P),
E = Glu,
D = Asp,
S = Ser,
A = Ala,
I = Ile,
Q = Gln,
M = Met,
V = Val,
P = Pro,
K = Lys,
L = Leu,
T = Thr,
G = Gly and
R = Arg.

EXAMPLE 3

Structural Studies Using Hydroxyapatite (HA)

Similarly, we investigated the adsorption of the CPP and synthetic homologues and analogues onto HA (Table 2).

These data also confirm that the Ser(P) cluster sequence is the major determinant for high affinity binding and that all three coutiguous Ser(P) residues are essential as loss of any one, even when substituted with a Glu or Asp, resulted in a considerably lower affinity contant K as shown in Table 2.

TABLE 2

CPP and Synthetic Peptide binding to HA at 37° C.

| | K ml/μmol | N μmol/m² | Molecular Area nm² |
|---|---|---|---|
| (SEQ ID NO: 1)$\alpha_{a1}$ (59–79) QMEAEΣIΣΣΣEEIVPNΣVEQK | 415 | 0.35 | 4.75 |
| (SEQ ID NO: 6)$\alpha_{a1}$ (63–70) EΣIΣΣΣEE | 10,370 | 0.47 | 3.56 |
| (SEQ ID NO: 5)$\alpha_{a1}$ (66–70) ΣΣΣEEE | 12,845 | 0.52 | 3.27 |
| (SEQ ID NO: 8)$\alpha_{a1}$ (71–78) IVPNΣVEQ | — | — | — |
| (SEQ ID NO: 7)$\alpha_{a1}$ (59–63) QMEAE | — | — | — |
| (SEQ ID NO: 5)ΣΣΣEE | 12,845 | 0.52 | 3.27 |
| (SEQ ID NO: 10)EΣΣEE | 1,513 | 0.96 | 1.74 |
| (SEQ ID NO: 11)DΣΣEE | 6,579 | 0.81 | 2.04 |
| (SEQ ID NO: 12)θθθEE | 12,234 | 0.51 | 3.27 |
| (SEQ ID NO: 21)TθθEE | 1,013 | 0.55 | 3.03 |
| (SEQ ID NO: 22)θTθEE | 837 | 0.44 | 3.77 |
| (SEQ ID NO: 23)θθTEE | 1,799 | 0.46 | 3.61 |

Σ = Ser(P),
θ = Thr(P)

Interestngly, repeating these HA adsorption experiments with salivary coated HA (sHA) revealed that the Ser(P) cluster motif was still the major determinant for adsorption although the affinities of the peptides for the sHA was slightly reduced by the presence of the salivary proteins. These results suggest that the predominant interaction of the CPP with pellicle and plaque is likely to be electrostatic and mediated by the Ser(P) cluster motif of the CPP.

We have also studied the docking of the peptide Ser(P)-Ser(P)- Ser(P)-Glu-Glu- onto three crystallographic planes of HA, {100}, {010} and {001} using computer simulation techniques and the unit cell coordinates of synthetic HA. These simulation studies revealed that the peptide -Ser(P)-Ser(P)- Ser(P)-Glu-Glu- is more likely to the {100} surface, followed by the {010} surface. The Ser(P)- cluster motif can therefore bind to both {100} and {010} surfaces thus allowing deposition of calcium, phosphate and hydroxyl ions on the {100} surface enabling growth of the HA crystal along the c-axis only. These results therefore can know explain the c-axis growth of HA crystals in enamel and dentine. Detailed examination of the computer simulation data shows that the -Ser(P)- Ser(P)- Ser(P)-Glu-Glu- conformer with the greatest relative binding energy is positioned on the HA surface such that the carboxyl groups of the glutamyl residues and the phosphoryl groups of the phosphoseryl residues are in proximity to the HA surface with maximal contact between these groups and surface calcium atoms.

EXAMPLE 4

Anticariogenic Activity of CPP-ACP in Human in situ Studies

The ability of the 1.0% w/v CPP-ACP pH 7.0 solution to prevent enamel demineralisation was studied in a human in situ caries model. The model consists of a removable appliance containing a left and right pair of enamel slabs placed to produce a plaque retention site. The inter-enamel plaque that developed (3–5 mg) was bacteriologically similar to normal supragingival plaque. On frequent exposure to sucrose solutions over a three week period, the increase in levels of mutans streptococci and lactobacilli and in sub-surface enamel demineralisation resulted in the formation of incipient "caries-like" lesions.

Two exposures of the CPP-ACP solution per day to the right pair of enamel slabs for 12 subjects produced a 51%±19% reduction in enamel mineral loss relative to the left-side, control enamel. The plaque exposed to the CPP-ACP solution contained 78±22 μmol/g calcium, 52±25 μmol/g $P_1$ and 2.4±0.7 mg/g CPP compared with 32±12 μmol/g calcium and 20±11 μmol/g $P_1$ in the control plaque. The level of the CPP was determined by competitive ELISA using an antibody that recognizes both $\alpha_{s1}$(59–79) and β(1–25). Electron micrographs of immunocytochemically stained sections of the plaque revealed localization of the peptide predominantly on the surface of microorganisms but also in the extracellular matrix.

Although these results indicate that CPP are incorporated into developing dental plaque, the actual level determined by ELISA would not be a true representation of that incorporated due to the breakdown of the CPP in plaque through the action of phosphatase and peptidase activities. The incorporation of the CPP-ACP in the plaque resulted in a 2.4 fold increase in the plaque calcium and a 2.6 fold increase in plaque $P_1$ with a Ca/$P_1$ ratio consistent with ACP.

EXAMPLE 5

Anticariogenic Potential of the CPP-ACP In a Mouthwash Study

A clinical trial of a mouthwash used thrice daily containing 3.0% CPP-ACP pH 9.0 showed that the calcium content of supragingival plaque (lower anterior teeth excluded) increased from 169±103 μmol/g dry weight to 610±234 μmol/g after use of the mouthwash for a three day period, and inorganic phosphate increased from 242±60 μmol/g dry weight to 551±164 μmol/g. These post-mouthwash levels of calcium and inorganic phosphate are the highest ever reported for non-mineralised supragingival plaque.

Without wishing to be bound by any proposed mechanism for the observed advantages, it is believed that the mechanism of anticariogenicity for the CPP-ACP is the incorporation of amorphous calcium phosphate in plaque, thereby depressing enamel demineralisation and enhancing remineralisation. In plaque, CPP-ACP would act as a reservoir of calcium and phosphate, buffering the free calcium and phosphate ion activities thereby helping to maintain a state of supersaturation with respect to tooth enamel. The binding of ACP to CPP is pH dependent with very little bound below pH 7.0.

EXAMPLE 6

Remineralisation of Enamel Lesions by CPP-ACP
A. In Vitro Studies

An in vitro enamel remineralisation system was used to study remineralisation of artificial lesions in human third molars by CPP-ACP solutions. Using this system, a 1.0% CPP-ACP solution replaced 56±21% of mineral lost. A 0.1% CPP-ACP solution replaced 34±18% of mineral lost. A further number of solutions containing various amounts of CPP (0.1–1.0%), calcium (6–60 mM) and phosphate (3.6–36 mM) at different pH values (7.0–9.0) were prepared. The associations between the activities of the various calcium phosphate species in solution and the rate of enamel lesion remineralisation for this series of solutions were then determined.

The activity of the neutral ion species $CaHO_4^\circ$ in the various remineralising solutions was found to be highly correlated with the rate of lesion remineralisation. The diffusion coefficient for the remineralisation process was estimated at $3\times10^{-10}$ $m^2s^{-1}$ which is consistent with the coefficients of diffusion for neutral molecules through a charged matrix. The rate of enamel remineralisation obtained with the 1.0% CPP-ACP solution was $3.3\times10^{-2}$ mol $HA/m^2/10$ days which is the highest remineralisation rate ever obtained. Calcium phosphate ions, in particular the neutral ion pa $CaHPO_4^{\circ}$, after diffusion into the enamel lesion, will dissociate and thereby increase the degree of saturation with respect to HA. The formation of HA in the lesion will lead to the generation of $H_3PO_4$, which being neutral itself, will diffuse out of the lesion down a concentration gradient.

The results indicate that the CPP-bound ACP, $CPP[Ca_3(PO_4)_{1.87}(HPO_4)_{0.2}xH_2O]_8$ acts as a reservoir of the neutral ion species, $CaHPO_4^{\circ}$ that is formed in the presence of acid. The acid can be generated by dental plaque bacteria; under these conditions, the CPP-bound ACP would buffer plaque pH and produce calcium and phosphate ions, in particular $CaHPO_4^{\circ}$. The increase in plaque $CaHPO_4^{\circ}$ would offset any fall in pH thereby preventing enamel demineralisation Acid is also generated in plaque as $H_3PO_4$ by the formation of HA in the enamel lesion during remineralisation. This therefore explains why the CPP-ACP solutions are such efficient remineralising solutions as they would consume the $H_3PO_4$ produced during enamel lesion remineralisation generating more $CaHPO_4^{\circ}$ thus maintaining its concentration gradient into the lesion. These results are therefore consistent with the proposed anticariogenic mechanism of the CPP being the inhibition of enamel demineralisation and enhancement of remineralisation through the localisation of ACP at the tooth surface.

B. Human in Situ Remineralisation Studies

The ability of CPP-ACP added to sugar-free (sorbitol) chewing gum to remineralise enamel sub-surface lesions was investigated in a randomized, cross-over, double-blind study. Ten subjects wore removable palatal appliances with six, human-enamel, half-slabs inset containing sub-race deminealised lesions. The other half of each enamel slab was stored in a humidified container and was used as the control deminealised lesion. There were four treatment groups in the study, sugar-free gum containing 3.0% w/w CPP-ACP, sugar-free gum containing 1.0% w/w CPP-ACP, sugar-free gum with no CPP-ACP and a no-gum-chewing control. The gums were chewed for 20 min periods, four times a day. The appliances were worn for this 20 min period and a further 20 min period after gum chewing. Each treatment was for 14 days duration and each of the ten subjects carried out each treatment with a one week rest between the treatments. At the completion of each treatment the enamel slabs were removed, paired with their respective deminealised control, embedded, sectioned and subjected to microradiography and computer-assisted densitometric image analysis to determine the level of remineralisation. The sugar-free gum treatment resulted in 9.82±1.81% remineralisation relative to the no-gum-chewing control whereas the gum containing 1.0% CPP-ACP produced 17.06±2.48% remineralisation and the 3.0% CPP-ACP gum produced 22.70±3.40% reminerlisation with all values being significantly different. These results showed that addition of 1.0% and 3.0% CPP-ACP to sugar-free gum produced a 74% and 131% increase respectively in sub-surface enamel remineralisation.

EXAMPLE 7

CPP-ACFP Mouthwash Study

A mouthwash study was conducted to determine the ability of a 3.0% CPP-ACFP mouthwash used thrice daily to increase supragingival plaque calcium, inorganic phosphate and fluoride ions. The 3.0% CPP-ACFP solution used as a mouthwash for four days contained 192 mM bound calcium ions, 120 mM bound phosphate ions and 24 mM (456 ppm) bound F ions stabilised by CPP. The use of the mouthwash resulted in a 1.9 fold increase in plaque calcium, a 1.5 fold increase in plaque phosphate and a dramatic 18 fold increase in plaque fluoride ion as shown in Table 3.

TABLE 3

Effect of CPP-ACFP on Plaque, Ca, $P_i$ and F Levels

|  | Ca $\mu mol/g$ | Pi $\mu mol/g$ | F $\mu mol/g$ |
| --- | --- | --- | --- |
| Control | 177 ± 53 | 306 ± 82 | 1.1 ± 0.9 |
| 3% CPP-ACFP | 336 ± 107 | 471 ± 113 | 19.9 ± 14.1 |
| 1000 ppm F | 158 ± 54 | 287 ± 29 | 1.9 ± 1.0 |
| 3% CaCPP | 193 ± 56 | 343 ± 102 | 1.5 ± 0.8 |

Although these marked increases in plaque calcium, phosphate and fluoride were found, dental calculus was not observed in any of the subjects, suggesting that the plaque calcium fluoride phosphate remained stabilised as the amorphous phase by the CPP and did not transform into a crystalline phase. These increases in the supragingival plaque levels of Ca, phosphate and fluoride ions produced by CPP-ACP are markedly greater than those obtained in a similar study using CaCPP and 1000 ppm F (MFP and NaF) toothpastes twice daily for a similar time period as indicated in Table 3. These results show a marked synergistic effect between fluoride ions and the CPP-ACP. This is particularly advantageous in view of the fact that the level of fluoride in oral compositions such as toothpaste can then be reduced, resulting in cost savings and lowered risk of fluorosis for individuals living in high-fluoride areas.

EXAMPLE 8

Interaction of CPP-ACP With Fluoride

An synergistic anticariogenic effect of the 1.0% CPP-ACP together with 500 ppm $F^{31}$ was observed in a rat caries model. Analysis of the solution containing 1.0% CPP, 60 mM $CaCl_2$, 36 mM sodium phosphate and 500 ppm F (26.3 mM NaF) pH 7.0 after ultrafiltration revealed that nearly half of the fluoride ion had incorporated into the ACP phase stabilised by the CPP to produce an amorphous calcium fluoride phosphate phase of composition $Ca_8(PO_4)_5F\ xH_2O$, with 24 Ca, 15 $PO_4$ and 3F molecules per CPP molecule.

Without wishing to be limited by any proposed mechanism for the observed beneficial effect, we consider that the anticariogenic mechanism of the CPP-ACP is the localisation of ACP at the tooth surface such that in the presence of acid, the ACP dissociates to release Ca and phosphate ions increasing the degree of saturation with sect to HA preventing enamel demineralisation and promoting remineralisation. The anticariogenic mechanism of fluoride is the localisation of the fluoride ion at the tooth surface, particularly in plaque in the presence of Ca and phosphate ions. This localisation increases the degree of saturation with respect to fluorapatite (FA) thus promoting remineralisation of enamel with FA. It is clear that for the formation of FA $[Ca_{10}(PO_4)_6F_2]$, calcium and phosphate ions must be co-localised in plaque at the tooth surface with the fluoride ion. The synergistic anticariogenic effect of CPP-ACP and F is therefore attributable to the localisation of ACFP at the tooth surface by the CPP which in effect would co-localise Ca, Pi and F.

This was demonstrated in the mouthwash study described in Example 7.

Metastable solutions of the CPP at pH 7.0 have been prepared containing amorphous calcium fluoride phosphate at remakably high concentrations. For example, a 10% w/v CPP -ACFP solution containing 640 mM Ca, 400 mM phosphate and 80 mM F (1,520 ppm F) at pH 7.0 has been prepared as well as a 20% CPP gel containing 1.28 M Ca, 800 mM phosphate and 160 mM F (3,040 ppm F$^-$) at pH 7.0. This solution and gel exhibit a significantly greater anticariogenicity relative to the fluoride alone, and therefore are superior additives to toothpastes and mouthwash and for professional application to improve the efficacy of the current fluoride-containing dentifrices and professionally-applied products.

Specific examples of formulations containing the complexes of the invention are provided below.

EXAMPLE 9

Toothpaste Formulations Containing CPP-ACFP

Formulation 1

| Ingredient | % w/w |
| --- | --- |
| Dicalcium phosphate dihydrate | 50.0 |
| Glycerol | 20.0 |
| Sodium carboxymethyl cellulose | 1.0 |
| Sodium lauryl sulphate | 1.5 |
| Sodium lauroyl sarconisate | 0.5 |
| Flavour | 1.0 |
| Sodium saccharin | 0.1 |
| Chlorhexidine gluconate | 0.01 |
| Dextranase | 0.01 |
| CPP-ACFP | 1.00 |
| Water | balance |

Formulation 2

| Ingredient | % w/w |
| --- | --- |
| Dicalcium phosphate dihydrate | 50.0 |
| Sorbitol | 10.0 |
| Glycerol | 10.0 |
| Sodium carboxymethyl cellulose | 1.0 |
| Sodium lauryl sulphate | 1.5 |
| Sodium lauroyl sarconisate | 0.5 |
| Flavour | 1.0 |
| Sodium saccharin | 0.1 |
| Sodium monofluorophosphate | 0.3 |
| Chlorhexidine gluconate | 0.01 |
| Dextranase | 0.01 |
| CPP-ACFP | 2.0 |
| Water | balance |

Formulation 3

| Ingredient | % w/w |
| --- | --- |
| Dicalcium phosphate dihydrate | 50.0 |
| Sorbitol | 10.0 |
| Glycerol | 10.0 |
| Sodium carboxymethyl cellulose | 1.0 |
| Lauroyl diethanolamide | 1.0 |
| Sucrose monolaurate | 2.0 |
| Flavour | 1.0 |
| Sodium saccharin | 0.1 |
| Sodium monofluorophosphate | 0.3 |
| Chlorhexidine gluconate | 0.01 |
| Dextranase | 0.01 |
| CPP-ACFP | 5.0 |
| Water | balance |

Formulation 4

| Ingredient | % w/w |
| --- | --- |
| Sorbitol | 22.0 |
| Irish moss | 1.0 |
| Sodium Hydroxide (50%) | 1.0 |
| Gantrez | 19.0 |
| Water (deionised) | 2.69 |
| Sodium Monofluorophosphate | 0.76 |
| Sodium saccharine | 0.3 |
| Pyrophosphate | 2.0 |
| Hydrated alumina | 48.0 |
| Flavour oil | 0.95 |
| CPP-ACFP | 1.0 |
| sodium lauryl sulphate | 2.00 |

Formulation 5

| Ingredient | % w/w |
| --- | --- |
| Sodium polyacrylate | 50.0 |
| Sorbitol | 10.0 |
| Glycerol | 20.0 |
| Flavour | 1.0 |
| Sodium saccharin | 0.1 |
| Sodium monofluorophosphate | 0.3 |
| Chlorhexidine gluconate | 0.01 |
| Ethanol | 3.0 |
| CPP-ACFP | 2.0 |
| Linolic acid | 0.05 |
| Water | balance |

EXAMPLE 10

Mouthwash Formulations

Formulation 1

| Ingredient | % w/w |
| --- | --- |
| Ethanol | 20.0 |
| Flavour | 1.0 |
| Sodium saccharin | 0.1 |
| Sodium monofluorophosphate | 0.3 |
| Chlorhexidine gluconate | 0.01 |
| Lauroyl diethanolamide | 0.3 |
| CPP-ACFP | 2.0 |
| Water | balance |

Formulation 2

| Ingredient | % w/w |
| --- | --- |
| Gantrez S-97 | 2.5 |
| Glycerine | 10.0 |

-continued

| Ingredient | % w/w |
|---|---|
| Flavour oil | 0.4 |
| Sodium monofluorophosphate | 0.05 |
| Chlorhexidine gluconate | 0.01 |
| Lauroyl diethanolamide | 0.2 |
| CPP-ACFP | 2.0 |
| Water | Balance |

EXAMPLE 11

Lozenge Formulation

| Ingredient | % w/w |
|---|---|
| Sugar | 75–80 |
| Corn syrup | 1–20 |
| Flavour oil | 1–2 |
| NaF | 0.01–0.05 |
| CPP-ACFP | 3.0 |
| Mg stearate | 1–5 |
| Water | balance |

EXAMPLE 12

Gingival Massage Cream Formulation

| Ingredient | % w/w |
|---|---|
| White petrolatum | 8.0 |
| Propylene glycol | 4.0 |
| Stearyl alcohol | 8.0 |
| Polyethylene Glycol 4000 | 25.0 |
| Polyethylene Glycol 400 | 37.0 |
| Sucrose monostearate | 0.5 |
| Chlorhexidine gluconate | 0.1 |
| CPP-ACFP | 3.0 |
| Water | balance |

EXAMPLE 13

Chewing Gum Formulation

| Ingredient | % w/w |
|---|---|
| Gum base | 30.0 |
| Calcium carbonate | 2.0 |
| Crystalline sorbitol | 53.0 |
| Glycerine | 0.5 |
| Flavour oil | 0.1 |
| CPP-ACFP | 2.0 |
| Water | balance |

EXAMPLE 14

Dietary Supplement

CPP-ACP was added at 1.0% w/w of the diet of rachitic chickens to determine the ability of the CPP-ACP to provide bioavailable calcium for bone accretion. CPP-ACP at 1.0% w/w in the diet produced a 34% reduction in the incidence of growth plate abnormalities, a 17% increase in tibial ash and a 22% reduction in the cartilaginous growth plate in the animals which was significantly greater than the CPP alone (Table 4) indicating that the CPP-ACP is superior to the CPP in providing bioavailable dietary calcium and in facilitating bone accretion.

TABLE 4

Effect of 1.0% CPP-ACP addition to the diet of rachitic chickens on incidence of growth plate abnormalities, tibial ash and cartilaginous growth plate width

|  | % Growth Abnormalities % | % Tibial Ash % | Growth Plate Width (mm) |
|---|---|---|---|
| Control | 53 ± 5 | 30 ± 2 | 5.4 ± 0.2 |
| 1.0% CPP | 47 ± 9 | 30 ± 2 | 5.3 ± 0.2 |
| 1.0% CPP-ACP | 35 ± 3 | 35 ± 1 | 4.2 ± 0.2 |

It should be understood that while the invention has been described in detail for the purposes of clarity and understanding, the examples were for illustrative purposes only. Other modifications of the embodiments of the present invention will be apparent to those skilled in the art of molecular biology, dental diagnostics, and related disciplines and are within the scope of the invention as describe

What is claimed is:

1. A stable, soluble calcium phosphate complex that is obtainable by a process comprising the steps of:
   (i) obtaining an solution of a phosphopeptide, wherein the phosphopeptide includes amino acid sequence Ser(P)-Ser(P)-Ser(P)-Glu-Glu (SEQ ID NO: 5);
   (ii) admixing, under alkaline conditions, the solution of step (i) with calcium ions and inorganic phosphate, to obtain a mixture; and
   (iii) isolating the complex from the mixture of step (ii).

2. The complex of claim 1, wherein the alkaline conditions are pH of about 9.

3. The complex of claim 1, wherein the amino acid sequence is selected from the group consisting of:
   (SEQ ID NO: 1) $Gln^{59}$-Met-Glu-Ala-Glu-Ser(P)-Ile-Ser(P)-Ser(P)-Ser(P)-Glu-Glu-Ile-Val-Pro-Asn-Ser(P)-Val-Glu-Gln-$Lys^{79}$ $\alpha_{s1}$(59–79);
   (SEQ ID NO: 2) $Arg^{1}$-Glu-Leu-Glu-Glu-Leu-Asn-Val-Pro-Gly-Glu-Ile-Val-Glu-Ser(P)-Leu-Ser(P)-Ser(P)-Ser(P)-Glu-Glu-Ser-Ile-Thr-$Arg^{25}$ $\beta$(1–25);
   (SEQ ID NO: 3) $Asn^{46}$-Ala-Asn-Glu-Glu-Glu-Tyr-Ser-Ile-Gly-Ser(P)-Ser(P)-Ser(P)-Glu-Glu-Ser(P)-Ala-Glu-Val-Ala-Thr-Glu-Glu-Val-$Lys^{70}$ $\alpha_{s2}$(46–70); and
   (SEQ ID NO: 4) $Lys^{1}$-Asn-Thr-Met-Glu-His-Val-Ser(P)-Ser(P)-Ser(P)-Glu-Glu-Ser-Ile-Ile-Ser(P)-Gln-Glu-Thr-Tyr-$Lys^{21}$ $\alpha_{s2}$(1–21).

4. The complex of claim 3, wherein the amino acid sequence is:
   (SEQ ID NO: 1) $Gln^{59}$-Met-Glu-Ala-Glu-Ser(P)-Ile-Ser(P)-Ser(P)-Ser(P)-Glu-Glu-Ile-Val-Pro-Asn-Ser(P)-Val-Glu-Gln-$Lys^{79}$ $\alpha_{s1}$(59–79).

5. A stable, soluble calcium fluoride phosphate complex that is obtainable by a process comprising the steps of:
   (i) obtaining a solution of a phosphopeptide, wherein the phosphopeptide includes amino acid sequence Ser(P)-Ser(P)-Ser(P)-Glu-Glu (SEQ ID NO: 5);
   (ii) admixing, under alkaline conditions, the solution of step (i) with calcium ions, inorgainc phosphate and fluoride ions, to obtain a mixture; and
   (iii) isolating the complex form the mixture of step (ii).

6. The complex of claim 5, wherein the alkaline conditions are pH of about 9.

7. The complex of claim 5, wherein the amino acid sequence is selected from the group consisting of:
   (SEQ ID NO: 1) $Gln^{59}$-Met-Glu-Ala-Glu-Ser(P)-Ile-Ser(P)-Ser(P)-Ser(P)-Glu-Glu-Ile-Val-Pro-Asn-Ser(P)-Val-Glu-Gln-$Lys^{79}$ $\alpha_{s1}$(59–79);
   (SEQ ID NO: 2) $Arg^{1}$-Glu-Leu-Glu-Glu-Leu-Asn-Val-Pro-Gly-Glu-Ile-Val-Glu-Ser(P)-Leu-Ser(P)-Ser(P)-Ser(P)-Glu-Glu-Ser-Ile-Thr-$Arg^{25}$ $\beta$(1–25);
   (SEQ ID NO: 3) $Asn^{46}$-Ala-Asn-Glu-Glu-Glu-Tyr-Ser-Ile-Gly-Ser(P)-Ser(P)-Ser(P)-Glu-Glu-Ser(P)-Ala-Glu-Val-Ala-Thr-Glu-Glu-Val-$Lys^{70}$ $\alpha_{s2}$(46–70); and
   (SEQ ID NO: 4) $Lys^{1}$-Asn-Thr-Met-Glu-His-Val-Ser(P)-Ser(P)-Ser(P)-Glu-Glu-Ser-Ile-Ile-Ser(P)-Gln-Glu-Thr-Tyr-$Lys^{21}$ $\alpha_{s2}$(1–21).

8. The complex of claim 7, wherein the amino acid sequence is:
   (SEQ ID NO: 1): $Gln^{59}$-Met-Glu-Ala-Glu-Ser(P)-Ile-Ser(P)-Ser(P)-Ser(P)-Glu-Glu-Ile-Val-Pro-Asn-Ser(P)-Val-Glu-Gln-$Lys^{79}$ $\alpha_{s1}$(59–79).

9. A method of preparing a stable, soluble calcium phosphate complex comprising the steps of:
   (i) obtaining a solution of a phosphopeptide, wherein the phosphopeptide includes amino acid sequence Ser(P)-Ser(P)-Ser(P)-Glu-Glu (SEQ ID NO: 5);
   (ii) admixing the solution of step (i) with calcium ions and inorganic phosphate at a pH of above 7, to obtain a mixture;
   (iii) filtering the mixture of step (ii) to produce a retentate, and drying the retentate to isolate the complex.

10. The method of claim 9, wherein step (ii) further comprises admixing the solution of step (i) with fluoride ions in addition to the calcium ions and inorganic phosphate.

11. A stable, soluble calcium phosphate complex that is obtainable by the process of claim 9.

12. A stable, soluble calcium phosphate complex that is obtainable by the process of claim 10.

13. A delivery vehicle for administering a complex of claim 1, 5, 11 or 12 to a target site, wherein the delivery vehicle is adapted to co-localize calcium and phosphate ions of the complex at the target site.

14. The delivery vehicle of claim 13 that is selected from the group consisting of toothpaste, toothpowder, liquid dentifrice, mouthwash, troche, chewing gum, dental paste, gingival massage cream, gargle tablet and foodstuff.

15. The delivery vehicle of claim 14, wherein the foodstuff is a dairy product.

16. A method of treating or preventing dental caries or tooth decay, comprising administering a complex according to claim 1, 5, 11 or 12 to the teeth or gums of a subject in need of such treatment.

17. A pharmaceutical composition comprising:
(i) a complex of claim 1, 6; and
(ii) a pharmaceutical carrier or a delivery vehicle.

18. The pharmaceutical composition of claim 17, wherein the complex is present in effective amount for remineralising teeth or for inhibiting cariogenesis or tooth decay in a subject.

19. The pharmaceutical composition of claim 17, wherein the complex is present in an effective amount for promoting calcium absorption in a subject suffering from a condition related to calcium loss, calcium deficiency or calcium malabsorption.

20. The pharmaceutical composition of claim 19, wherein the condition is osteoporosis or osteomalacia.

21. The pharmaceutical composition of claim 17, further comprising foodstuff.

22. The pharmaceutical composition of claim 21, wherein the foodstuff is a dairy product.

23. The pharmaceutical composition of claim 17, further comprising a dentifrice.

24. The pharmaceutical composition of claim 23, wherein the dentifrice is selected from the group consisting of toothpaste, toothpowder, liquid dentifrice, mouthwash, troche, chewing gum, dental paste, gingival massage cream and gargle tablet.

25. A method for remineralising teeth or for inhibiting cariogenesis or tooth decay, comprising administering an effective amount of a complex of claim 1, 5, 11 or 12 to a subject in need thereof.

26. A method for promoting calcium absorption in a subject suffering from a condition related to calcium loss, calcium deficiency or calcium malabsorption, comprising administering an effective amount of a complex of claim 1, 5, 11 or 12 to the subject.

27. The method of claim 26, wherein the condition is osteoporosis or osteomalacia.

* * * * *

SEQUENCE LISTING

```
<160> NUMBER OF SEQ ID NOS: 23

<210> SEQ ID NO 1
<211> LENGTH: 21
<212> TYPE: PRT
<213> ORGANISM: Bos sp.
<220> FEATURE:
<221> NAME/KEY: misc_feature
<222> LOCATION: (6)..(6)
<223> OTHER INFORMATION: Xaa is a phosphorylated Serine
<221> NAME/KEY: misc_feature
<222> LOCATION: (8)..(8)
<223> OTHER INFORMATION: Xaa is a phosphorylated Serine
<221> NAME/KEY: misc_feature
<222> LOCATION: (9)..(9)
<223> OTHER INFORMATION: Xaa is a phosphorylated Serine
<221> NAME/KEY: misc_feature
<222> LOCATION: (10)..(10)
<223> OTHER INFORMATION: Xaa is a phosphorylated Serine
```

```
<221> NAME/KEY: misc_feature
<222> LOCATION: (17)..(17)
<223> OTHER INFORMATION: Xaa is a phosphorylated Serine

<400> SEQUENCE: 1

Gln Met Glu Ala Glu Xaa Ile Xaa Xaa Xaa Glu Glu Ile Val Pro Asn
1               5                   10                  15

Xaa Val Glu Gln Lys
            20

<210> SEQ ID NO 2
<211> LENGTH: 25
<212> TYPE: PRT
<213> ORGANISM: Bos sp.
<220> FEATURE:
<221> NAME/KEY: misc_feature
<222> LOCATION: (15)..(15)
<223> OTHER INFORMATION: Xaa is a phosphorylated Serine
<221> NAME/KEY: misc_feature
<222> LOCATION: (17)..(17)
<223> OTHER INFORMATION: Xaa is a phosphorylated Serine
<221> NAME/KEY: misc_feature
<222> LOCATION: (18)..(18)
<223> OTHER INFORMATION: Xaa is a phosphorylated Serine
<221> NAME/KEY: misc_feature
<222> LOCATION: (19)..(19)
<223> OTHER INFORMATION: Xaa is a phosphorylated Serine

<400> SEQUENCE: 2

Arg Glu Leu Glu Glu Leu Asn Val Pro Gly Glu Ile Val Glu Xaa Leu
1               5                   10                  15

Xaa Xaa Xaa Glu Glu Ser Ile Thr Arg
            20                  25

<210> SEQ ID NO 3
<211> LENGTH: 25
<212> TYPE: PRT
<213> ORGANISM: Bos sp.
<220> FEATURE:
<221> NAME/KEY: misc_feature
<222> LOCATION: (11)..(11)
<223> OTHER INFORMATION: Xaa is a phosphorylated Serine
<221> NAME/KEY: misc_feature
<222> LOCATION: (12)..(12)
<223> OTHER INFORMATION: Xaa is a phosphorylated Serine
<221> NAME/KEY: misc_feature
<222> LOCATION: (13)..(13)
<223> OTHER INFORMATION: Xaa is a phosphorylated Serine
<221> NAME/KEY: misc_feature
<222> LOCATION: (16)..(16)
<223> OTHER INFORMATION: Xaa is a phosphorylated Serine

<400> SEQUENCE: 3

Asn Ala Asn Glu Glu Glu Tyr Ser Ile Gly Xaa Xaa Xaa Glu Glu Xaa
1               5                   10                  15

Ala Glu Val Ala Thr Glu Glu Val Lys
            20                  25

<210> SEQ ID NO 4
<211> LENGTH: 21
<212> TYPE: PRT
<213> ORGANISM: Bos sp.
<220> FEATURE:
<221> NAME/KEY: misc_feature
<222> LOCATION: (8)..(8)
<223> OTHER INFORMATION: Xaa is a phosphorylated Serine
<221> NAME/KEY: misc_feature
<222> LOCATION: (9)..(9)
<223> OTHER INFORMATION: Xaa is a phosphorylated Serine
<221> NAME/KEY: misc_feature
```

```
<222> LOCATION: (10)..(10)
<223> OTHER INFORMATION: Xaa is a phosphorylated Serine
<221> NAME/KEY: misc_feature
<222> LOCATION: (16)..(16)
<223> OTHER INFORMATION: Xaa is a phosphorylated Serine

<400> SEQUENCE: 4

Lys Asn Thr Met Glu His Val Xaa Xaa Xaa Glu Glu Ser Ile Ile Xaa
1               5                   10                  15

Gln Glu Thr Tyr Lys
            20

<210> SEQ ID NO 5
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic peptide
<221> NAME/KEY: misc_feature
<222> LOCATION: (1)..(1)
<223> OTHER INFORMATION: Xaa is a phosphorylated Serine
<221> NAME/KEY: misc_feature
<222> LOCATION: (2)..(2)
<223> OTHER INFORMATION: Xaa is a phosphorylated Serine
<221> NAME/KEY: misc_feature
<222> LOCATION: (3)..(3)
<223> OTHER INFORMATION: Xaa is a phosphorylated Serine

<400> SEQUENCE: 5

Xaa Xaa Xaa Glu Glu
1               5

<210> SEQ ID NO 6
<211> LENGTH: 8
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic peptide
<221> NAME/KEY: misc_feature
<222> LOCATION: (2)..(2)
<223> OTHER INFORMATION: Xaa is a phosphorylated Serine
<221> NAME/KEY: misc_feature
<222> LOCATION: (4)..(4)
<223> OTHER INFORMATION: Xaa is a phosphorylated Serine
<221> NAME/KEY: misc_feature
<222> LOCATION: (5)..(5)
<223> OTHER INFORMATION: Xaa is a phosphorylated Serine
<221> NAME/KEY: misc_feature
<222> LOCATION: (6)..(6)
<223> OTHER INFORMATION: Xaa is a phosphorylated Serine

<400> SEQUENCE: 6

Glu Xaa Ile Xaa Xaa Xaa Glu Glu
1               5

<210> SEQ ID NO 7
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic peptide

<400> SEQUENCE: 7

Gln Met Glu Ala Glu
1               5
```

<210> SEQ ID NO 8
<211> LENGTH: 8
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic peptide
<221> NAME/KEY: misc_feature
<222> LOCATION: (5)..(5)
<223> OTHER INFORMATION: Xaa is a phosphorylated Serine

<400> SEQUENCE: 8

Ile Val Pro Asn Xaa Val Glu Gln
1               5

<210> SEQ ID NO 9
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic peptide
<221> NAME/KEY: misc_feature
<222> LOCATION: (2)..(2)
<223> OTHER INFORMATION: Xaa is a phosphorylated Serine
<221> NAME/KEY: misc_feature
<222> LOCATION: (3)..(3)
<223> OTHER INFORMATION: Xaa is a phosphorylated Serine

<400> SEQUENCE: 9

Ser Xaa Xaa Glu Glu
1               5

<210> SEQ ID NO 10
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic peptide
<221> NAME/KEY: misc_feature
<222> LOCATION: (2)..(2)
<223> OTHER INFORMATION: Xaa is a phosphorylated Serine
<221> NAME/KEY: misc_feature
<222> LOCATION: (3)..(3)
<223> OTHER INFORMATION: Xaa is a phosphorylated Serine

<400> SEQUENCE: 10

Glu Xaa Xaa Glu Glu
1               5

<210> SEQ ID NO 11
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic peptide
<221> NAME/KEY: misc_feature
<222> LOCATION: (2)..(2)
<223> OTHER INFORMATION: Xaa is a phosphorylated Serine
<221> NAME/KEY: misc_feature
<222> LOCATION: (3)..(3)
<223> OTHER INFORMATION: Xaa is a phosphorylated Serine

<400> SEQUENCE: 11

```
Asp Xaa Xaa Glu Glu
1               5

<210> SEQ ID NO 12
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic peptide
<221> NAME/KEY: misc_feature
<222> LOCATION: (1)..(1)
<223> OTHER INFORMATION: Xaa is a phosphorylated Threonine
<221> NAME/KEY: misc_feature
<222> LOCATION: (2)..(2)
<223> OTHER INFORMATION: Xaa is a phosphorylated Threonine
<221> NAME/KEY: misc_feature
<222> LOCATION: (3)..(3)
<223> OTHER INFORMATION: Xaa is a phosphorylated Threonine

<400> SEQUENCE: 12

Xaa Xaa Xaa Glu Glu
1               5

<210> SEQ ID NO 13
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic peptide
<221> NAME/KEY: misc_feature
<222> LOCATION: (2)..(2)
<223> OTHER INFORMATION: Xaa is a phosphorylated Threonine
<221> NAME/KEY: misc_feature
<222> LOCATION: (3)..(3)
<223> OTHER INFORMATION: Xaa is a phosphorylated Threonine

<400> SEQUENCE: 13

Ser Xaa Xaa Glu Glu
1               5

<210> SEQ ID NO 14
<211> LENGTH: 4
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic peptide
<221> NAME/KEY: misc_feature
<222> LOCATION: (2)..(2)
<223> OTHER INFORMATION: Xaa is a phosphorylated Serine

<400> SEQUENCE: 14

Ala Xaa Ala Glu
1

<210> SEQ ID NO 15
<211> LENGTH: 6
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic peptide
<221> NAME/KEY: misc_feature
<222> LOCATION: (3)..(3)
<223> OTHER INFORMATION: Xaa is a phosphorylated Serine
```

```
<400> SEQUENCE: 15

Ile Ala Xaa Ala Glu Ala
1               5

<210> SEQ ID NO 16
<211> LENGTH: 8
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic peptide
<221> NAME/KEY: misc_feature
<222> LOCATION: (5)..(5)
<223> OTHER INFORMATION: Xaa is a phosphorylated Serine

<400> SEQUENCE: 16

Glu Ala Ile Ala Xaa Ala Glu Ala
1               5

<210> SEQ ID NO 17
<211> LENGTH: 6
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic peptide
<221> NAME/KEY: misc_feature
<222> LOCATION: (2)..(2)
<223> OTHER INFORMATION: Xaa is a phosphorylated Serine
<221> NAME/KEY: misc_feature
<222> LOCATION: (4)..(4)
<223> OTHER INFORMATION: Xaa is a phosphorylated Serine

<400> SEQUENCE: 17

Ala Xaa Ala Xaa Ala Glu
1               5

<210> SEQ ID NO 18
<211> LENGTH: 8
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic peptide
<221> NAME/KEY: misc_feature
<222> LOCATION: (2)..(2)
<223> OTHER INFORMATION: Xaa is a phosphorylated Serine
<221> NAME/KEY: misc_feature
<222> LOCATION: (4)..(4)
<223> OTHER INFORMATION: Xaa is a phosphorylated Serine
<221> NAME/KEY: misc_feature
<222> LOCATION: (6)..(6)
<223> OTHER INFORMATION: Xaa is a phosphorylated Serine

<400> SEQUENCE: 18

Ala Xaa Ala Xaa Ala Xaa Ala Glu
1               5

<210> SEQ ID NO 19
<211> LENGTH: 10
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic peptide
<221> NAME/KEY: misc_feature
<222> LOCATION: (2)..(2)
```

```
<223> OTHER INFORMATION: Xaa is a phosphorylated Serine
<221> NAME/KEY: misc_feature
<222> LOCATION: (4)..(4)
<223> OTHER INFORMATION: Xaa is a phosphorylated Serine
<221> NAME/KEY: misc_feature
<222> LOCATION: (6)..(6)
<223> OTHER INFORMATION: Xaa is a phosphorylated Serine
<221> NAME/KEY: misc_feature
<222> LOCATION: (8)..(8)
<223> OTHER INFORMATION: Xaa is a phosphorylated Serine

<400> SEQUENCE: 19

Ala Xaa Ala Xaa Ala Xaa Ala Xaa Ala Glu
1               5                   10

<210> SEQ ID NO 20
<211> LENGTH: 8
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic peptide
<221> NAME/KEY: misc_feature
<222> LOCATION: (2)..(2)
<223> OTHER INFORMATION: Xaa is a phosphorylated Serine
<221> NAME/KEY: misc_feature
<222> LOCATION: (4)..(4)
<223> OTHER INFORMATION: Xaa is a phosphorylated Serine
<221> NAME/KEY: misc_feature
<222> LOCATION: (5)..(5)
<223> OTHER INFORMATION: Xaa is a phosphorylated Serine
<221> NAME/KEY: misc_feature
<222> LOCATION: (6)..(6)
<223> OTHER INFORMATION: Xaa is a phosphorylated Serine

<400> SEQUENCE: 20

Glu Xaa Leu Xaa Xaa Xaa Glu Glu
1               5

<210> SEQ ID NO 21
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic peptide
<221> NAME/KEY: misc_feature
<222> LOCATION: (2)..(2)
<223> OTHER INFORMATION: Xaa is a phosphorylated Threonine
<221> NAME/KEY: misc_feature
<222> LOCATION: (3)..(3)
<223> OTHER INFORMATION: Xaa is a phosphorylated Threonine

<400> SEQUENCE: 21

Thr Xaa Xaa Glu Glu
1               5

<210> SEQ ID NO 22
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic peptide
<221> NAME/KEY: misc_feature
<222> LOCATION: (1)..(1)
<223> OTHER INFORMATION: Xaa is a phosphorylated Threonine
<221> NAME/KEY: misc_feature
<222> LOCATION: (3)..(3)
<223> OTHER INFORMATION: Xaa is a phosphorylated Threonine
```

```
<400> SEQUENCE: 22

Xaa Thr Xaa Glu Glu
1               5

<210> SEQ ID NO 23
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic peptide
<221> NAME/KEY: misc_feature
<222> LOCATION: (1)..(1)
<223> OTHER INFORMATION: Xaa is a phosphorylated Threonine
<221> NAME/KEY: misc_feature
<222> LOCATION: (2)..(2)
<223> OTHER INFORMATION: Xaa is a phosphorylated Threonine

<400> SEQUENCE: 23

Xaa Xaa Thr Glu Glu
1               5
```